Figure 1:
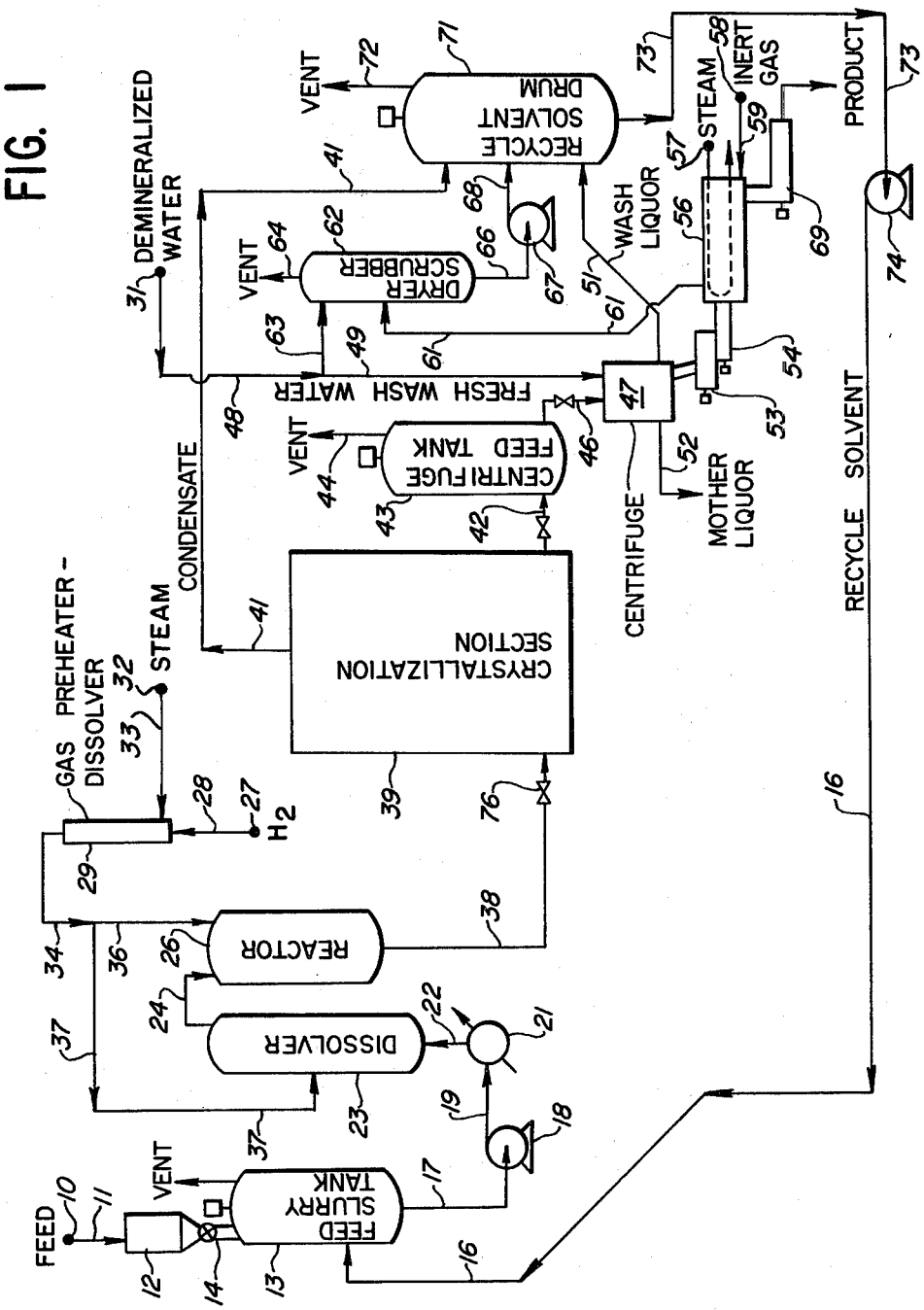

United States Patent [19]

Stech et al.

[11] 4,405,809

[45] Sep. 20, 1983

[54] PROCESS FOR THE MANUFACTURE OF AROMATIC POLYCARBOXYLIC ACIDS HAVING DELTA Y VALUES BELOW TEN

[75] Inventors: Eric N. Stech, Mount Pleasant, S.C.; Mark S. Montgomery, Homewood, Ill.; J. Frederick Bates, Mount Pleasant, S.C.

[73] Assignee: Standard Oil Company (Indiana), Chicago, Ill.

[21] Appl. No.: 327,606

[22] Filed: Dec. 4, 1981

[51] Int. Cl.$^3$ .............................................. C07C 51/42
[52] U.S. Cl. .................................. 562/487; 562/412; 562/485
[58] Field of Search ........................ 562/412, 485, 487

[56] References Cited

U.S. PATENT DOCUMENTS

| | | | |
|---|---|---|---|
| 3,151,154 | 9/1964 | Sargent et al. | 562/487 |
| 3,456,001 | 7/1969 | Olsen | 562/487 |
| 3,522,298 | 7/1970 | Bryant et al. | 562/487 |
| 3,546,285 | 12/1970 | Witt | 562/487 |
| 3,584,039 | 6/1971 | Meyer | 562/487 |
| 3,639,465 | 2/1972 | Olsen et al. | 562/487 |
| 4,126,638 | 11/1978 | Alagy et al. | 562/487 |
| 4,260,817 | 4/1981 | Thompson et al. | 562/487 |

Primary Examiner—Natalie Trousof
Assistant Examiner—Vera C. Clarke
Attorney, Agent, or Firm—Gunar J. Blumberg; William H. Magidson; William T. Magidson

[57] ABSTRACT

A process for purifying aromatic polycarboxylic acid produced by liquid phase catalytic oxidation of polyalkyl aromatic hydrocarbon to remove undesirable aldehyde aromatic carboxylic acid and other impurities including the step of contacting an aqueous solution of said impure acid and hydrogen with a noble metal-containing catalyst, our improvement comprising eliminating any gas phase during the contacting step and conducting said contacting step with said aqueous solution by maintaining hydrogen at about 10 to about 75 percent of saturation in the liquid reaction medium to produce purified aromatic polycarboxylic acid having delta Y values below ten.

10 Claims, 1 Drawing Figure

PROCESS FOR THE MANUFACTURE OF AROMATIC POLYCARBOXYLIC ACIDS HAVING DELTA Y VALUES BELOW TEN

FIELD OF THE INVENTION

This invention relates to the purification of polycarboxylic aromatic acids, and more particularly concerns the preparation of polycarboxylic aromatic acid having a purity sufficient for direct esterification with diols to produce super polyesters. The process of the present invention is applicable to purification of polycarboxylic aromatic acids such as, for example, terephthalic, trimesic, isophthalic, naphthalene dicarboxylic, trimellitic, mellitic, etc. The process is described herein as applied to the purification of crude terephthalic acid to produce terephthalic acid of fiber-grade quality, however, this should not be deemed a limitation of the process.

BACKGROUND

High molecular weight polyesters of terephthalic acid with various diols find extensive use as Dacron, Terylene, Kodel, and Vycron fibers, and Mylar film. These super polyesters, first described in U.S. Pat. No. 2,465,319 to Whinfield and Dickson, in the past have been prepared from dimethylterephthalate, which is trans-esterified with the appropriate diol, such as ethylene glycol, and then polycondensed to form the super polyester. Polyester preparation via dimethylterephthalate has been considered an essential step by reason of the exceptionally high purity requirements imposed on the polyester.

With the advent of improved processes for the manufacture of terephthalic acid, much attention has been directed to obtaining polyesters by direct esterification of terephthalic acid with the diol.

This has manifest advantages of simplicity and economy as compared with the dimethylterephthalate route. As yet, however, there remains serious difficulty in obtaining terephthalic acid of suitable purity. Unless the initial terephthalic acid is virtually completely free from extraneous contaminants, the polyester will have too low a melting point and will be of unsatisfactory color.

It is an object of this invention to reduce the hydrogen used in aromatic carboxylic acid purification and to produce purified products having delta Y values below ten. Another object is to use hydrogen in an amount calculated to be between about ten and seventy-five percent of saturation of the aqueous reaction medium. Using less than full hydrogen saturation of the reaction medium prevents upsets in the catalyst which increase the delta Y values to an unacceptable level. Excess hydrogen usage is a safety risk and can cause reaction upsets which produce product having very high delta Y values, certainly values above ten, the maximum values acceptable to obtain commercially polyesters by direct esterification of terephthalic acid with ethyleneglycol. Additional advantages of the novel process are reduced hydrogen usage and improved catalyst life and activity. A further object is to avoid in our novel process, a gas phase in the catalyst bed, particularly a flash vaporization to the gas phase. This is critical in preventing reactor upsets and increasing the delta Y values above 10 and higher which are unacceptable in the manufacture of polyesters.

It is believed that purified terephthalic acid impurities are carbon particles which give high delta Y values. The main contributor of carbon particles is likely to be the charcoal used to support the nobel metal catalyst. The test for delta Y values is given in the analytic procedures section of this specification. Other impurities are the compound 4-carboxybenzaldehyde, an intermediate formed when terephthalic acid is obtained from the oxidation of paraxylene or other para-disubstituted alkyl benzene, is known to be deleterious with respect to polyester quality. Other impurities are unidentified color bodies, of the benzil or fluoronone structure, usually present as trace byproducts of most terephthalic acid production processes, and yield off-color polyesters. However, any method of purifying terephthalic acid must produce a product having delta Y value below 10.

It is disclosed in U.S. Pat. No. 3,639,465, granted Feb. 1, 1972, that terephthalic acid of a purity suitable for direct esterification with a diol to produce films and fibers may be obtained from the impure terephthalic acid by catalytical hydrogen treatment in polar solvent solution, preferable aqueous solution, of the impure acid under liquid phase conditions preferably by percolating the solution and hydrogen or mixture of hydrogen and inert gas through a bed of catalyst particles having noble metal hydrogenation catalyst. The improvement afforded by our novel process over U.S. Pat. No. 3,639,465 is the contacting of the catalyst with the solution of aromatic polycarboxylic acid and hydrogen dissolved in the solvent with a noble metal-containing catalyst so that no gaseous phase is present in the catalyst bed and that the liquid phase has a hydrogen concentration of about 10 to 75 of saturation, preferably about 40 to 60 percent.

When any gas or mixture of gas and vapor comes in contact with a pure liquid (that is liquid having no dissolved gas) the gas or soluble component of a gaseous mixture will dissolve in the liquid. If this contact is maintained for a sufficient length of time, equilibrium is attained. Regardless of the duration of contact between the liquid and gas, after equilibrium is reached no more gas will dissolve into the liquid phase. The liquid is then said to be saturated with the particular gas at the given conditions. For the given conditions saturation is the highest equilibrium concentration of gas which will dissolve in the liquid. When less than this equilibrium amount of gas is dissolved in the liquid the situation is called partial saturation. Percent of saturation is 100 multiplied by the ratio of the amount of gas dissolved to the amount of gas which would be dissolved at equilibrium where the amount of dissolved gas is measured in volume units of gas per mass of liquid solution at reference conditions. For example 100 percent of saturation is about 0.6 cc of hydrogen per gram of solution at a temperature of about 525° F. and a hydrogen pressure of about 150 psia above an aqueous solution pressure containing about 9.1 weight percent terephthalic acid. When the aqueous solution contains about 23.1 weight percent terephthalic acid, 100 percent of saturation increases to about 0.77 cc of hydrogen per gram of solution. The reference state for the hydrogen volumes is 32° F. and 1 atms.

In the prior art, including U.S. Pat. No. 3,639,465, the hydrogenation is conducted in such a manner that the reactor feed is fully saturated and an excess gaseous phase is present in the reactor. The disadvantage of prior art procedure is that the palladium charcoal catalyst tends to be crushed and small carbon particles are introduced into the final purified terephthalic acid product. This carbon contamination of the purified terephthalic acid is measured as a delta Y. For example fine carbon particles added to purified terephthalic acid at a level of only 1 ppm increases delta Y value to more than twenty. A commercially acceptable product should have a delta Y below 10. When the hydrogenation of the terephthalic acid impurities are conducted in the manner according to this invention, wherein hydrogen saturation of the reaction medium is kept at about 10 to about 75 percent of saturation, delta values below 10 are obtained. In the best mode for conducting our process the hydrogen concentration of about 40 to about 60 percent of saturation in the liquid is maintained without having any gaseous phase present in the catalyst.

According to the present invention, there is provided a process for purifying aromatic polycarboxylic acid produced by liquid phase catalytic oxidation of polyalkyl aromatic hydrocarbons to remove carbon particles and undesirable aldehyde and other impurities comprising the steps of forming an aqueous solution of said acid containing said impurities in water, contacting said solution and hydrogen at about 10 to about 75 percent of saturation of the liquid medium with a noble metal-containing catalyst, and recovering purified acid having delta values below 10. This process is particularly well suited for purification of aromatic dicarboxylic acids, for example, purifying crude terephthalic acid. The recovering of purified acid is conveniently effected by crystallizing the acid from the hydrogen treated aqueous solution, wherein the hydrogen in the reaction medium is in the range of about 10 to about 75 percent of saturation of the aqueous solution. The noble metal-containing catalyst suitably comprises charcoal having supported thereon 0.01 to 1 percent by weight of the noble metal. Preferably the charcoal support is one having a surface area in the range of about 1,000 to 2,000 square meters per gram. Particularly desirable noble metals for use as the catalyst are platinum and palladium, preferably palladium.

The present invention also provides a method of purifying crude aromatic polycarboxylic acid obtained by catalytic liquid phase oxidation of a polyalkyl aromatic hydrocarbon with molecular oxygen in the presence of a heavy metal oxidation catalyst said aromatic hydrocarbon having at least two nuclear alkyl hydrocarbon substituents whose carbon attached to the nuclear aromatic carbon has at least one hydrogen atom, which crude aromatic polycarboxylic acid has an aromatic polycarboxylic acid content of at least 99.0 percent by weight, preferably 99.5 weight percent, and which has as its principal impurity a carboxy aromatic aldehyde corresponding to said aromatic polycarboxylic acid, which method comprises forming an aqueous liquid solution of said crude acid in water, contacting said solution in the liquid phase at a temperature in the range of about 450°–600° F. with hydrogen at about 10 to about 75 percent of saturation of the reaction medium with a noble metal-containing hydrogenation catalyst for a time sufficient to effect substantial reduction of said aldehyde and without introducing carbon impurities and recovering purified acid having delta Y values of less than 10.

According to a preferred embodiment of the present invention there is provided a method of producing fiber-grade terephthalic acid from crude terephthalic acid obtained by catalytic liquid phase oxidation of paraxylene with molecular oxygen in the presence of a heavy metal oxidation catalyst, which crude terephthalic acid has a terephthalic acid content of at least 99.0 percent by weight, preferably 99.5 weight percent, and which has as its principal impurity 4-carboxybenzaldehyde, which method comprises forming a solution of said crude terephthalic acid in water, contacting said solution in the liquid phase at a temperature in the range of about 450° to 600° F. and hydrogen mixture at about 10 to about 75 percent of saturation of the reaction medium with a noble metal-charcoal hydrogenation catalyst for a time sufficient to effect substantial reduction of said aldehyde to para-toluic acid and recovering fiber-grade terephthalic acid by crystallization having delta Y values below 10.

When terephthalic acid, or other aromatic discarboxylic acid to be employed in super polyester production, is purified by the process of the present invention it is said to be of "fiber-grade" quality. The term "fiber-grade" does not denote a quantitative degree of purity, but rather describes a terephthalic acid which is sufficiently free from 4-carboxybenzaldehyde and has a delta Y value below 10 to yield a super polyester upon direct esterification with a diol which is satisfactory for the intended purpose.

The process of the present invention has particular application to purification of terephthalic acid produced by the liquid phase air (molecular oxygen) oxidation of paraxylene using a heavy metal and bromine as catalyst as described in Saffer et al. U.S. Pat. No. 2,833,816. The process of the present invention may also be used to advantage for purification of terephthalic acid from other processes for the catalytic liquid phase oxidation of para-dialkylbenzenes with molecular oxygen in the presence of heavy metal oxidation catalyst, also promoted with acetaldehyde or methyl ethyl ketone, for the terephthalic acids produced by these oxidation processes also contain 4-CBA impurity. Terephthalic acid from any source which contains 4-carboxybenzaldehyde and which is yellowish in color, can be converted to fiber grade terephthalic acid by the process of this invention.

The process of the invention is conducted at elevated temperature and pressure while the terephthalic acid or other aromatic polycarboxylic acid is dissolved in an inert polar solvent. Examples of suitable solvents include the lower molecular weight alkyl carboxylic acids and water, with water being the preferred solvent. By reason of its low solubility in water, terephthalic acid requires either large volumes of water or high temperatures in order for the desired terephthalic acid production quantity to be put into solution. For reasons of economic equipment design and process operation, it is therefore desirable to conduct the process within the range of about 392° to about 700° F., although lower or higher temperatures may be used in particular circumstances. The most advantageous temperature range is about 440°–575° F., e.g. 464°–550° F. The quantity of water needed to dissolve the terephthalic acid at various temperatures may be estimated from the table below:

TABLE I

| Terephthalic acid, g./100g.H$_2$O | Temperature, °F. for solution |
|---|---|
| 1 | 365 |
| 5 | 401 |
| 10 | 468 |
| 20 | 498 |

TABLE I-continued

| Terephthalic acid, g./100g.H$_2$O | Temperature, °F. for solution |
|---|---|
| 30 | 522 |

For the purification of crude terephthalic acid aqueous solution temperatures in the range of 450° to 600° F. are preferred because these solutions carry more than 5 pounds of the acid per 100 pounds of water.

Pressure conditions for the process of this invention depend upon the temperature at which this process is conducted. Since the temperature at which significant amounts of the impure terephthalic acid may be dissolved in water are substantially above the normal boiling point of water, and since the hydrogenation section of the process of this invention is to be carried out with the solvent in the liquid phase, the pressure will necessarily be substantially above atmospheric pressure.

Hydrogen treating time, or space velocity, will depend on the initial terephthalic acid purity, that is, the amount of impurity to be reduced, on the desired fiber-grade specifications imposed on the purified terephthalic acid, and on other conditions of the hydrogenation such as for example, catalyst activity. Ordinarily a treating time, i.e. contact time with the catalyst, within the range of about 0.001 to about 10 hours, advantageously about 0.01 to 2 hours, will suffice for most operations. Although treating time is not a critical variable, it must be taken into consideration with regard to the aforementioned severe hydrogenation and its side effects.

The hydrogenation catalyst required for the process of this invention to convert the aldehyde carbonyl group on the 4-carboxybenzaldehyde (4-CBA) at least to a methylol group, e.g. to convert the 4-CBA to p-methylol benzoic acid, and to destroy, or otherwise render innocuous, other impurities present (e.g. those of benzil and fluorenone structure) in the feed terephthalic acid is preferably a Group VIII noble metal, preferably platinum and/or palladium, supported on adsorbent, high surface area charcoal. A wide variety of catalysts have been found efficacious, and while carbon-supported noble metals are outstanding, reference may be made to any of the standard texts on hydrogenation or catalysts for alternative materials which are catalytically effective under aqueous phase hydrogenation conditions. It must be kept in mind, however, that the catalyst used must be one which is useful for effecting the hydrogenation under mild hydrogenation conditions as defined herein. Numerous catalysts are listed, for example, in Kirk and Othmer's "Encyclopedia of Chemical Technology" (Interscience), particularly the chapters on Hydrogenation and Catalysts; Emmett's "Catalysis", (Reinhold), particularly Volumes IV and I on Hydrogenation; Lohse's "Catalytic Chemistry" (Chemical Publishing Company), particularly the sections on Group VIII Metal Catalysts; and such patents as U.S. Pat. Nos. 2,070,770 and 2,105,664. Illustrative catalysts include the Group VIII Noble Metals Ruthenium, Rhodium, Palladium, Osmium, Irridium, and Platinum, advantageously extended on a support such as activated carbon, e.g. adsorbent charcoal.

The noble metal hydrogenation catalyst for use in the inventive process must have sufficient hydrogenation activity to convert the aldehyde carbonyl group on the 4-carboxybenzaldehyde at least to a methylol group, e.g. p-methylol benzoic acid, and to destroy, or otherwise render innocuous, other impurities present in the feed terephthalic acid. Noble metal supported on adsorbent charcoal in the amount of 0.01–1.0 weight percent, based on total catalyst, is suitable as the hydrogenation catalyst. Advantageously, nobel metal contents in the range of about 0.05–0.5 weight percent may be used, with about 0.3–0.7 weight percent being the preferred noble metal content for use in trickle beds of catalyst. The higher noble metal contents tend to produce over-hydrogenation while the lesser amounts suffer some loss in hydrogenation activity as compared with catalysts of the preferred noble metal content.

The adsorbent charcoal support for the noble metal may be any such support which has sufficient mechanical strength and surface area. It has been sound that palladium-charcoal catalysts having a palladium content in the preferred range of 0.3–0.7 weight percent and also having a very high surface in the range of about 1000–3000 square meters per gram of catalyst are particularly well suited for use in the present invention.

Turning now to the drawings, FIG. 1, is a simplified schematic flow plan of a preferred embodiment of the invention. It is to be understood that this embodiment is for the purpose of illustration and are not to be regarded as a limitation of the scope of the present invention.

Referring now to FIG. 1, dry crude terephthalic acid (TA) feed (e.g. containing 0.5 to 1.0 percent by weight 4-carboxybenzaldehyde) from source 10, such as for example a storage silo, is transferred via line 11 into crude terephthalic weight hopper 12. Crude terephthalic acid is fed from the weight hopper at a constant rate into the feed slurry tank 13 by the crude terephthalic feeder 14 which suitably can be any solids transfer feeder such as, for example, a Star feeder. The crude terephthalic feeder 14 sets the nominal feed rate to the process. Recycled water from line 16 is added to feed slurry tank 13 on flow control to provide a slurry concentration of crude TA in water of approximately 15–35 weight percent, preferably about 20–30 weight percent, and in this example about 23.1 weight percent total solids. Demineralized water is preferred as solvent water. Slurry hold-up in feed slurry tank 13 of about 45 minutes at normal level is sufficient to dampen out fluctuations in the TA and water feed rates to the tank. The temperature in feed slurry tank 13 is maintained at a temperature in the range of about 100°–300° F., preferably about 200° F. and the pressure is conveniently near atmospheric at temperatures below the boiling point of water by venting to the atmosphere. Feed slurry tank 13 is provided with an agitator to contact the solid crude TA and the recycled water in order to maintain a uniform slurry.

Slurry is withdrawn from feed slurry tank 13 via line 17 and transferred via high-pressure pump 18 via line 19 through preheater 21. Preheater 21 is conveniently a shell-and-tube exchanger with one or two tube pass. Normally the tube-side velocity of the slurry feed is sufficient to keep the slurry in suspension. Suitable preheater outlet conditions of temperature and pressure are about 525° to about 530° F. and about 985 p.s.i.a., respectively. The preheater slurry is passed via line 22 into dissolver 23.

The reactor feed stream is passed up-flow through the dissolver 23 which provides a residence time of approximately 20 minutes. A clear solution of TA in water overflows from the dissolver 23 via line 24 to the hydrogenation reactor 26. This solution, when formed from a slurry of approximately 23.1 weight percent solids, contains about 30 pounds of crude TA per 100 pounds of water at about 525° to about 530° F. and 985 p.s.i.a. The precipitation (crystallization) point for this solution is about 522° F.

Crude terephthalic acid solution from line 24 flows continuously into the hydrogenation reactor 26. The bed is supported by a screen about equivalent to 8-gauge Tyler mesh.

Hydrogen from source 27, is passed via line 28 into gas preheater-dissolver 29. Steam and hot condensate from source 32 is also passed via line 33 into gas preheater-dissolver 29 wherein the hydrogen-containing gas is heated to reaction temperature. The stream from the preheater-dissolver is passed via lines 34 and 36 into the top section of the reactor 26 so that hydrogen is dissolved in the solution and thus is readily available to effect hydrogenation upon contact with the catalyst in the center section of reactor 26.

Since the TA solution is highly corrosive at reactor effluent temperature, careful selection of suitable corrosion resistant elements is required.

Reactor effluent is passed via line 38 and inlet valve 76 to crystallization section 39. In the crystallization section, water is removed from the hot TA solution by high rate evaporative cooling. As a result of both the cooling and the solvent removal, TA crystallizes from solution. Evaporated water is condensed and the condensate is withdrawn from the crystallization section and passed via line 41 into recycle solvent drum 71. The slurry of TA crystals resulting from the crystallization is withdrawn from the crystallization section via line 42 and passed into centrifuge feed tank 43 which is vented to the atmosphere by line 44. The centrifuge feed tank 43 is provided with an agitator to maintain the slurry of TA crystals on suspension. The TA slurry is passed from the centrifuge feed tank 43 via valved line 46 into one or more centrifuges 47 wherein the crystals are separated from the mother liquor and the crystals washed with fresh demineralized wash water obtained from source 31 via lines 48 and 49. Wash water from the centrifuge is passed via line 51 into the recycle solvent drum 71. Mother liquor is withdrawn from the centrifuge and discarded via line 52. Purified TA crystals from the centrifuge 47 are withdrawn from the centrifuge and fed via auger feeders 53 and 54 into rotary kiln crystal dryer 56 which is heated by steam from source 57. Inert gas, such as nitrogen, from source 58 may be passed via line 59 into and through drying kiln 56 to assist in removing moisture from the TA crystals. The product is dried to a moisture content of about 0.05 weight percent water. Inert gas and water vapor containing some TA fines are withdrawn from the kiln 56 and passed via line 61 into dryer-scrubber 62 wherein the gases are washed countercurrently by a stream of fresh demineralized water. The water is introduced to the dryer-scrubber 62 from source 31 via lines 48 and 63 and descends countercurrently to the rising gas stream removing TA fines from the gases which are vented from the scrubber via line 64. Water containing TA fines is withdrawn from the dryer-scrubber 62 and passed via lines 66, pump 67 and line 68 into the recycle solvent drum 71. The solvent drum is vented to the atmosphere via line 72. An agitator is provided within the solvent recycle drum 71 in order to maintain undissolved particles of TA, primarily from scrubber 62, in suspension. Recycle solvent water is withdrawn from the recycle solvent drum 71 and passed via line 73, pump 74, and line 16 into the feed slurry tank 13. Dried purified TA product is withdrawn from the drying kiln 56 and passed via conveyor 69 to storage.

Utilizing the improvements of this invention and practicing it as shown in FIG. 1 which comprise conducting the contacting with catalyst step in the absence of a gas phase, particularly a flash vaporization to a gas phase, with aqueous solution having hydrogen dissolved at about 10 to 75 percent of saturation to produce purified terephthalic acid having delta Y values below 10 gave the results summarized in Table II.

TABLE II

| Run No. (Monthly Average) | % Conversion of 4CBA | delta Y |
|---|---|---|
| 1 | 99.4 | 3.7 |
| 2 | 99.5 | 2.8 |
| 3 | 99.4 | 3.3 |
| 4 | 99.5 | 2.4 |
| 5 | 99.5 | 2.6 |
| 6 | 99.6 | 2.4 |

ANALYTICAL PROCEDURE FOR DELTA Y DETERMINATIONS

This procedure measures the amount of ammonium hydroxide insolubles by light reflectance from a membrane filter used to filter an ammonia solution of PTA. The tristimulus color Y value for the sample filter and a blank filter are determined and the difference in values, expressed as delta Y, is a measure of the particulate contamination in PTA.

A 40 g sample of PTA is dissolved in 550 ml of prefiltered dilute ammonium hydroxide solution and this PTA solution is filtered through a 0.22 micron porosity MF Millipore filter. The filter is mounted on a 2"×2" glass slide for support and the tristimulus color Y value of the residue is determined on a color meter. The Y value of a blank filter is also determined and the difference between the sample and the blank is reported as delta Y. A delta Y of less than 10 is considered acceptable. A visual inspection of the filter can be made to identify the nature of the contaminants.

The Y value is a measure of greyness and as such any dark colored contaminants are detected easily, such as catalyst fines, oxidation reactor burn carbon, rust and metal salts. Lighter colored materials such as alumina and glass do not contrast with the white filter and are, therefore, not readily detected. Visual identification of insoluble material may be made to help determine the source of contamination.

Iron in some forms will contribute a brown "stain" on the filter. If such a stain is observed, the tristimulus color b value may be determined as a measure of this form of contaminant.

Table III

The following apparatus is used in determining delta Y values:

1. Gardner XL-10 Color Difference Meter, Catalog Number CG 6533 (Gardner Laboratory Inc., P.O. Box 5728, 5521 Landy Lane, Bethesda, Md., 20014); or equivalent instrument which will determine tristimulus color Y values.
2. Sample plate for color meter with 1⅜ inch aperture. Gardner Instrument Company will supply this plate for their instrument on request.
3. Standard color plate for the instrument used, Gardner Catalog Number CG 6810, Series GS 69.

4. Filter assembly; Pyrex Millipore filter apparatus, Catalog Number XX1004700. Millipore Corporation, Bedford, Mass., 01730.
5. Filters; MF Millipore filters, 0.22 micron porosity, 47 mm diam., Millipore Catalog Number GSWP04700.
6. Forceps; smooth, flat tipped, Millipore Catalog Number XX6200006.
7. Magnetic Stirrer; any brand is suitable but one having capabilities of multiple position stirring is preferred, to enable running several samples simultaneously. EX: Cole Parmer "Magne-4," Catalog Number 4820-10; Cole Parmer, 7425 N. Park Ave., Chicago, Ill., 60648.
8. Erlenmeyer flasks, 1000 ml capacity, Kimax Number 4980 or equivalent, several required.
9. Beakers, 150 ml capacity, several required.
10. Petri dishes, several required.
11. Wash bottles; 1000 ml polyethylene squeeze type are suitable. Two required.
12. Solvent storage containers; 5 gallon polyethylene containers with spigot. This item is optional but is convenient when large quantities of solvents are used.
13. Watch glasses, 70–80 mm diam., several required.
14. Graduated cylinders, 1000 ml and 250 ml.
15. Vacuum filtration flasks, 1000 ml, several required.

Table IV

The following reagents are used to determine the delta Y values:

1. Distilled or deionized water.
2. Filtered water; filter through a 0.22 micron porosity MF filter and store in a polyethylene container.
3. Concentrated ammonium hydroxide, 0.90 sp. gr.
4. Filtered dilute ammonium hydroxide; dilute 127 ml of conc. ammonium hydroxide to 1000 ml with water and mix thoroughly to obtain about 3.7 wt. percent $NH_3$. It is preferred to allow this solution to stand overnight before filtration to allow complete precipitation of impurity metals. Filter through a 0.22 micron filter prior to use and store in a polyethylene container, with suitable protection to avoid contamination by particulate matter in the atmosphere.

If metal contaminants in the water are high, the filter will "blind-off" quickly. In this event, a larger porosity filter placed on top of the 0.22 micron filter will minimize this problem. Polyvic filters having 2.0 micron porosity (millipore Catalog Number BSWD04700) have been found to be very useful in this application.

The procedure for determining delta Y values is set forth hereinbelow:

40 g±0.5 g of well-mixed sample is weighed into a 150 ml beaker. 550 ml of filtered, dilute ammonium hydroxide is placed in a 1000 ml Erlenmeyer flask, along with a clean magnetic stirring bar. With the stirrer set for fast agitation, the PTA sample is trickled into the ammonium hydroxide solution. The Erlenmeyer flask is covered with a beaker immediately after addition of the sample is complete. When the sample is nearly dissolved, it is washed down the sides of the Erlenmeyer flask with dilute ammonia. Stirring is continued until the sample is completely dissolved.

The sample solution is poured into the filter and vacuum is then applied. The filter assembly is covered with a petri dish. Care is taken not to allow the filter disk to become dry at any time during filtration. 200 ml of filtered water is added to the Erlenmeyer and swirled to wash down the sides and this wash is added to the solution in the filter funnel.

When the filtration is nearly complete, the sides of the filter funnel are washed down with filtered water.

The color meter is standarized using the standard plate and the large beam setting on the instrument, the Gardner XL-10 Color Differences Meter described above.

The dry, mounted filter disk is centered over the aperture, making sure that only the residue is illuminated. The glass slide is covered with a large bottle cap or similar device to exclude all external light. It is important that the covering device should not come in direct contact with the glass slide.

The Y value is measured and recorded.

Calculation delta $Y = Y$ blank $- Y$ sample

A delta Y of greater than 10 indicates that the sample is heavily contaminated and that it is not a commercially accepted product.

What is claimed is:

1. In a process for purifying aromatic polycarboxylic acid produced by liquid phase catalytic oxidation of polyalkyl aromatic hydrocarbon to remove undesirable aldehyde aromatic carboxylic acid and other impurities including the step of contacting a water solution of said impure acid and hydrogen gas with a noble metal-containing catalyst; the improvement comprising eliminating any gas phase during the contacting step and conducting said contacting step with said water solution by maintaining hydrogen at about 10 to about 75 percent of saturation in the liquid reaction medium to produce purified aromatic polycarboxylic acid having delta Y values below ten.

2. In a process for purifying aromatic polycarboxylic acid produced by liquid phase catalytic oxidation of polyalkyl aromatic hydrocarbon to remove undesirable aldehyde aromatic carboxylic acid and other impurities including the step of contacting a water solution of said impure acid and hydrogen gas with a noble metal-containing catalyst; the improvement comprising eliminating any gas phase during the contacting step and conducting said contacting step with said water solution by maintaining hydrogen at about 40 to about 60 percent of saturation in the liquid reaction medium to produce purified aromatic polycarboxylic acid having delta Y values below ten.

3. In a process for purifying terephthalic acid produced by liquid phase catalytic oxidation of paraxylene to remove undesirable aldehyde aromatic carboxylic acid and other impurities including the step of contacting a water solution of said impure acid and hydrogen gas with a noble metal-containing catalyst; the improvement comprising eliminating any gas phase during the contacting step and conducting said contacting step with said water solution by maintaining hydrogen at about 10 to about 75 percent of saturation in the liquid reaction medium to produce purified aromatic polycarboxylic acid have delta Y values below ten.

4. In a process for purifying terephthalic acid produced by liquid phase catalytic oxidation of paraxylene to remove undesirable aldehye aromatic carboxylic acid and other impurities including the step of contacting a water solution of said impure acid and hydrogen gas with a noble metal-containing catalyst; the improvement comprising eliminating any hydrogen gas phase during the contacting step and conducting said contacting step with said water solution by maintaining hydrogen at about 10 to about 75 percent of saturation in the liquid reaction medium to produce purified aromatic polycarboxylic acid having delta Y values below ten.

5. In a process for purifying terephthalic acid produced by liquid phase catalytic oxidation of paraxylene to remove undesirable aldehyde aromatic carboxylic acid and other impurities including the step of contacting a water solution of said impure acid and hydrogen gas with a noble metal-containing catalyst; the improvement comprising eliminating any gas phase during the contacting step and conducting said contacting step with said water solution by maintaining hydrogen at about 40 to about 60 percent of saturation in the liquid reaction medium to produce purified aromatic polycarboxylic acid having delta Y values below ten.

6. In a process for purifying terephthalic acid produced by liquid phase catalytic oxidation of paraxylene to remove undesirable aldehyde aromatic carboxylic acid and other impurities including the step of contacting a water solution of said impure acid and hydrogen gas with a noble metal-containing catalyst; the improvement comprising eliminating any hydrogen gas phase during the contacting step and conducting said contacting step with said water solution by maintaining hydrogen at about 40 to about 60 percent of saturation in the liquid reaction medium to produce purified aromatic polycarboxylic acid having delta Y values below ten.

7. In a continuous process for purifying terephthalic acid produced by liquid phase catalytic oxidation of paraxylene to remove undesirable aldehyde aromatic carboxylic acid and other impurities including the step of contacting a water solution of said impure acid and hydrogen gas with a noble metal-containing catalyst; the improvement comprising eliminating any gas phase during the contacting step and conducting said contacting step with said water solution by maintaining hydrogen at about 10 to about 75 percent of saturation in the liquid reaction medium to produce purified aromatic polycarboxylic acid having delta Y values below ten.

8. In a continuous process for purifying terephthalic acid produced by liquid phase catalytic oxidation of paraxylene to remove undesirable aldehyde aromatic carboxylic acid and other impurities including the step of contacting a water solution of said impure acid and hydrogen gas with a noble metal-containing catalyst; the improvement comprising eliminating any hydrogen gas phase during the contacting step and conducting said contacting step with said water solution by maintaining hydrogen at about 10 to about 75 percent of saturation in the liquid reaction medium to produce purified aromatic polycarboxylic acid having delta Y values below ten.

9. In a continuous process for purifying terephthalic acid produced by liquid phase catalytic oxidation of paraxylene to remove undesirable aldehyde aromatic carboxylic acid and other impurities including the step of contacting a water solution of said impure acid and hydrogen gas with a noble metal-containing catalyst; the improvement comprising eliminating any gas phase during the contacting step and conducting said contacting step with said water solution by maintaining hydrogen at about 40 to about 60 percent of saturation in the liquid reaction medium to produce purified aromatic polycarboxylic acid having delta Y values below ten.

10. In a continuous process for purifying terephthalic acid produced by liquid phase catalytic oxidation of paraxylene to remove undesirable aldehyde aromatic carboxylic acid and other impurities including the step of contacting a water solution of said impure acid and hydrogen gas with a noble metal-containing catalyst; the improvement comprising eliminating any hydrogen gas phase during the contacting step and conducting said contacting step with said water solution by maintaining hydrogen at about 40 to about 60 percent of saturation in the liquid reaction medium to produce purified aromatic polycarboxylic acid having delta Y values below ten.

* * * * *

UNITED STATES PATENT OFFICE
CERTIFICATE OF CORRECTION

Patent No. 4,405,809          Dated September 20, 1983

Inventor(s) Eric N. Stech, Mark S. Montgomery and J. Frederick Bates

It is certified that error appears in the above-identified patent and that said Letters Patent are hereby corrected as shown below:

| Col. | Line | | |
|---|---|---|---|
| 2 | 1 | "nobel metal" and should read | --noble metal-- |
| 4 | 14-15 | "discarboxylic" and should read | --dicarboxylic-- |
| 5 | 60 | "VIII Hoble" and should read | --VIII Noble-- |
| 6 | 15 | "sound that" and should read | --found that-- |

Signed and Sealed this

Third Day of April 1984

[SEAL]

Attest:

GERALD J. MOSSINGHOFF

Attesting Officer      Commissioner of Patents and Trademarks